United States Patent [19]

Laurent et al.

[11] Patent Number: 5,040,895

[45] Date of Patent: Aug. 20, 1991

[54] PROCESS FOR THE SIMULTANEOUS DETECTION OF SEVERAL GASES IN A GASEOUS MIXTURE, AND EQUIPMENT FOR USING THE PROCESS

[75] Inventors: Dominique Laurent, Lyons; Gerard Fortunato, Vienne, both of France

[73] Assignee: Societe Nationale Elf Aquitaine, Courbevoie, France

[21] Appl. No.: 440,267

[22] Filed: Nov. 22, 1989

[30] Foreign Application Priority Data

Nov. 25, 1988 [FR] France .................................. 88 15456

[51] Int. Cl.$^5$ .............................................. G01B 9/02
[52] U.S. Cl. ..................................... 356/346; 356/352
[58] Field of Search ................................ 356/346, 352

[56] References Cited

U.S. PATENT DOCUMENTS 3,909,132  9/1975  Barrett .......................... 356/352 X
4,718,765  1/1988  Fortunato et al. ............. 356/352 X Primary Examiner—Davis L. Willis
Assistant Examiner—Matthew W. Koren

[57] ABSTRACT

Process and interferometric device for detecting and measuring the concentration, in a single operation, of all gases, having almost periodic absorption structures, contained in a gaseous mixture, each of the gases being associated with a characteristic path difference. Luminous flux is analyzed after passage through a cell containing the mixture, using to a multiple-wave interferometer, for example, a Fabry-Perrot interferometer, in which the inside faces of plates therein are highly reflective, and one of which plates is displaceable at a constant speed, it thus being possible to sweep a very wide range of path difference. Analysis of the output signal is performed frequency band by frequency band, by seeking the maximum.

7 Claims, 2 Drawing Sheets

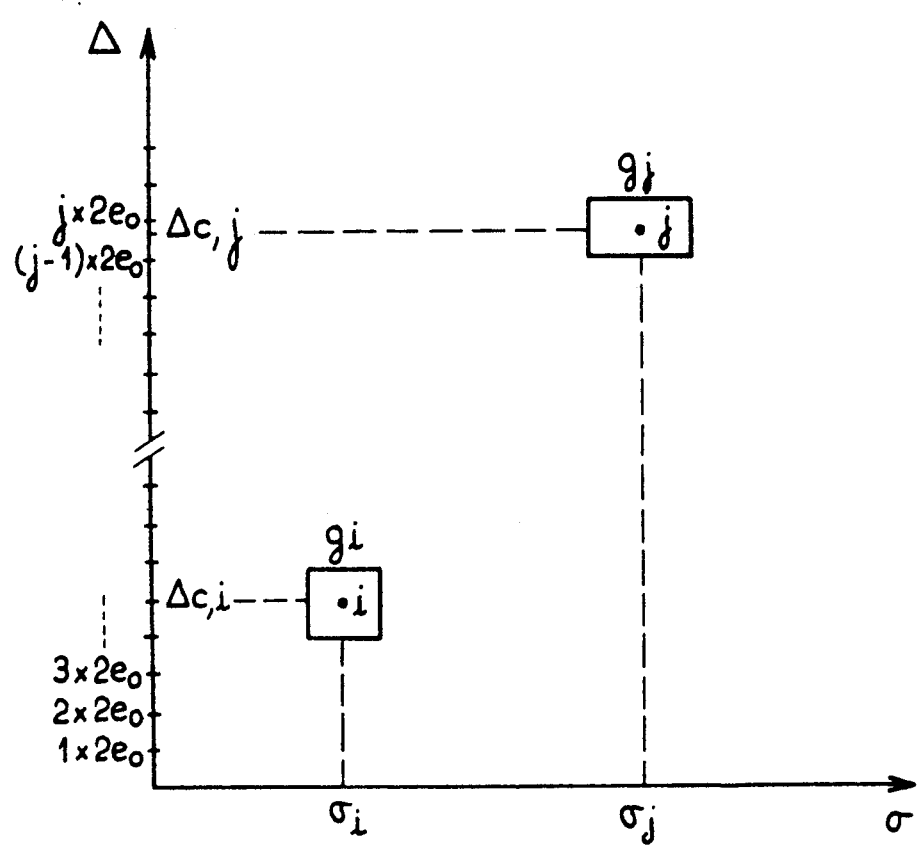
FIG_3

PROCESS FOR THE SIMULTANEOUS DETECTION OF SEVERAL GASES IN A GASEOUS MIXTURE, AND EQUIPMENT FOR USING THE PROCESS

FIELD OF THE INVENTION

The present invention relates to a process for simultaneously detecting in a gaseous mixture several gases, each exhibiting a quasi periodic absorption structure, such being the case with a very large number of gases, in particular industrial pollutants such as $NO_2$, $SO_2$, $NO$, $H_2S$, $CO$, $CO_2$, $N_2O$.

This invention also relates to equipment for using such a process.

BACKGROUND OF THE INVENTION

The system of fringes of the interferogram of the absorption spectrum of one of the gases, which it is desired to detect, exhibits a periodicity $\delta\sigma$, measured in wave number. The process standardly used for detection of such a gas consists in using an interferometer set on a path difference adapted to the gas to be studied. In general, the interferogram of a luminous flux having passed through a cell containing the gas to be studied, and the interferometer characterized by a path difference $\Delta_c$ will exhibit a maximum of contrast of the fringes for $\Delta_c = 1/\delta\sigma$.

French patent FR-A-2,555,747 describes a device making it possible to use such a process and to detect a gas exhibiting a quasi periodic absorption spectrum. This prior device comprises a light source whose beam goes successively through a concentration lens, a gas cell containing the gaseous mixture to be studied, an interference filter suitable for isolating the total of the specific absorption spectral band of the studied gas, a Fabry-Perrot interferometer consisting of two plates that are separated by a distance e and whose opposite faces are plane and parallel and each covered by a thin layer whose reflecting power is slight, at most 0.5, over a broad spectral region, and a detector delivering a signal whose maximum amplitude is proportional to the concentration of the studied gas contained in the mixture of the cell.

In this invention of the prior art, the Fabry-Perrot interferometer is used as a 2-wave interferometer, i.e., reflection coefficients of the inside faces of the interferometer plates are slight enough for an incident ray I reaching the interferometer to give rise to only two rays T0 and T1 in which almost the total of the energy of the incident ray is found, primary ray T0 being transmitted directly and indirect ray T1 being reflected once.

The absorption region of a gas studied corresponds to a well-defined path difference of the interferometer, and therefore to a distance between the interferometer plates characteristic of the gas.

In the invention of the prior art, it is possible to adapt at best the distance between the plates, to find one that corresponds to the particular gas studied and which leads to a maximum signal, by moving at least one of the plates of the interferometer with the help of piezoelectric ceramics supplied with direct current.

In a preferred embodiment of the prior art, the 2nd plate of the interferometer is mounted on piezoelectric cells supplied with alternating current, so that the distance between the plates varies between $e - \delta e$ and $e + \delta e$ at a frequency f linked to that of the current. This operation has the sole purpose of modulating the output signal, the modulation being understood here by the repetition, at frequency f of a portion in the vicinity of its maximum, of the intensity curve as a function of the interplate distance, to allow a more precise reading of this maximum.

In another device of the prior art, the Fabry-Perrot interferometer is replaced by an interferometry and modulation unit consisting of a polarizing film acting as a polarizer, a birefringent plate with thickness $e'$ and birefringence $\Delta n$ providing a path difference $\Delta_c = e' \times \Delta n$, another polarizing film acting as an analyzer, the width of the birefringent plate being selected as a function of its birefringence so that a maximum signal is collected on the detector for the spectrum of the gas to be identified.

These devices, considering existing materials that can be used, are not excessively costly and make it possible to process gases exhibiting a fine absorption structure in the spectral region between 0.1 and 5 microns.

Such devices exhibit a great specificity because it is necessary, for a second gas to provide a signal that absorbs in the same wavelength region defined by the filter and with a periodicity very close to that of the gas for whose study the device is more particularly adapted.

SUMMARY OF THE INVENTION

While preserving the advantages of the devices of the prior art, the invention makes it possible to limit their drawbacks, particularly the specificity of the equipment as a function of the gas to be studied. The device and process proposed according to the present invention have the object of using an interferometer and modulation unit simultaneously providing several distinct path differences, and allowing the modulation of the interference states corresponding to these path differences at different frequencies, for the detection of several gases in a gaseous mixture. This object is achieved by use of a device comprising a light source, a concentration lens, a cell containing the mixture to be analyzed, a multiple-wave interferometer, for example a Fabry-Perrot interferometer in which at least one of the plates therein can be displaced longitudinally at a constant speed, and wherein opposite faces of the plates therein are covered with a reflecting layer with a reflection coefficient greater than 0.5, and a detector.

The present invention makes possible the detection of all the gases having a quasi-periodic absorption structure, contained in the mixture, in a single operation; likewise, thanks to the present invention, use of an entire array of equipment, each specific for a particular gas is avoided.

BRIEF DESCRIPTION OF THE DRAWINGS

Other characteristics and advantages of this invention will come out more clearly from reading the following description given with reference to the accompanying figures in which:

FIG. 3 is a theoretical representation of the signal obtained in the diagram $\Delta\sigma$.

DETAILED DESCRIPTION OF THE INVENTION

The process according to the present invention consists of the following steps: making a light beam with a broad spectrum pass through the gaseous mixture to be analyzed, in creating—at the level of the interferometer and from the incident light beam after it has gone through the gaseous mixture—numerous, at least three, rays transmitted parallel, the vibrations carried by these rays each exhibiting, relative to those of the directly transmitted ray, a path difference which is a different multiple of an elementary path difference $\Delta_c$; modulating the vibrations of each of these rays transmitted at different frequencies by making the elementary path difference vary regularly by displacing one of the plates of the interferometer at a constant speed; of focusing these transmitted rays; detecting and recording the signal resulting from the superposition of vibrations associated with different transmitted and modulated rays and in analyzing this signal, after frequency filtering, so that the analysis of the signal, that is of its intensity, is made frequency band by frequency band, the frequency bands being contiguous.

Figure 2:
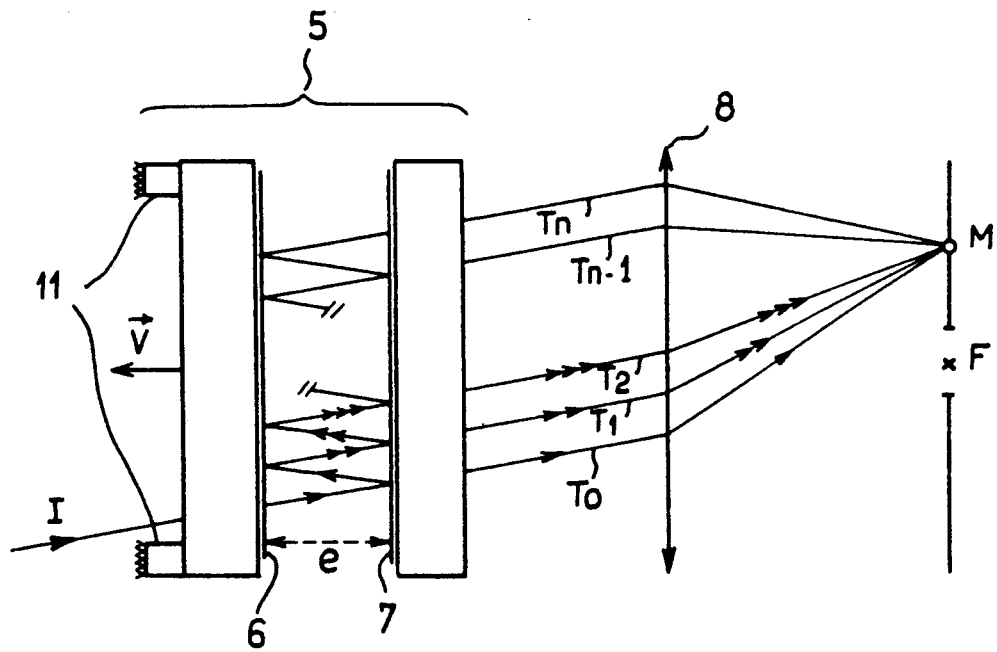
FIG. 2 represents diagrammatically the interferometry and modulation unit of the invention according to a preferred embodiment and its operating principle.

Such a process can be used thanks to a multiple-wave interferometer such as a Fabry-Perrot interferometer, as diagrammed in FIG. 2, whose opposite plane and parallel faces are covered with a thin layer whose reflecting power is greater than 0.5, for example 0.95. A ray incident on such a plate, one of whose faces exhibits a reflection coefficient R, has part of its energy reflected by the reflecting layer and the other part transmitted through the plate. The phenomena are such that if the amplitude of the incident ray is equal to 1, the amplitude of the reflected ray will be equal to R, the amplitude of the transmitted ray will be equal to T, the energy of the reflected ray will be equal to $R^2$, and of the energy the transmitted ray equal to $T^2$, the sum of the two energies of the transmitted and reflected rays being equal to the energy of the incident ray. If the amplitude of the incident ray on a reflecting layer with coefficient R is R, the ray reflected by this layer will be of amplitude equal to $R_2$ and the ray transmitted by a layer of the same characteristic placed in the path of this reflected ray with amplitude $R_2$ will be of amplitude $R^2T$.

The two parallel and plane plates of a Fabry-Perrot interferometer whose two inside faces, spaced at distance e, are covered by a fine reflecting layer which it will be assumed, for simplification—but this is not a limitation—is of the same strong reflecting coefficient R, with preferably R greater than 0.9, constitutes a sort of energy trap and a system such that an incident ray, on entering the system, gives rise to several transmitted rays, parallel to incident ray I, and with amplitude T, RT ... $R^{n-1}T$ for the ray of order n, where R and T respectively represent the reflecting power and transmission power of the layers deposited on the two faces of opposite plates; the vibrations of the transmitted rays exhibiting, relative to the incident ray, path differences $\Delta_c, 2\Delta_c, \ldots (n-1)\Delta_c$, respectively, for the ray of order n, which will be taken into account in a phase term.

If a convergent lens is placed behind the multiple-wave interferometric system, the vibrations carried by each of these rays parallel to the output of the interferometer are superposed at a point M of the focal plane of the lens.

The resulting amplitude of these vibrations which are superposed at point M of the focal plane of the lens will be, $\sigma$ being the number of waves $$A = T + R\ T\ e^{-2\pi j\sigma\Delta c} + R^2\ T\ e^{-2\pi j\sigma\cdot 2\Delta c} + \ldots + R^{n-1}\ T\ e^{-2\pi j\sigma(n-1)\Delta c}$$

and the intensity $$I = A.A^* = T^2\ (1 + R\ e^{-2\pi j\sigma\Delta c} + R^2\ e^{-2\pi j\sigma\cdot 2\Delta c} + \ldots + R^{n-1}\ e^{-2\pi j\sigma(n-1)\Delta c} + \ldots) \times (1 + R\ e^{2\pi j\sigma\Delta c} + R^2\ e^{2\pi j\sigma 2\Delta c} + \ldots + R^{n-1}\ e^{2\pi j\sigma(n-1)\Delta c})$$

by correctly grouping the terms and assuming $$1 + R^2 + R^4 + \ldots + R^{2a} + \ldots = \frac{1}{1-R^2}$$

there is found $$I = \frac{T^2}{1-R^2}\ [1 + 2R\cos 2\pi\sigma\Delta_c + \ldots + 2R^n\cos 2\pi\sigma n\Delta_c]$$

which is the decomposition as a sinusoidal function of the Airy function, the most current form of representation of the intensity provided by a Fabry-Perrot interferometer.

For point F of the focal plane located in the optical axis, the path difference characterizing the rays focused at F is $\Delta_c = 2e$ where e represents the thickness of the layer of air between the two parallel and plane plates of the Fabry-Perrot interferometer. This thickness e can be made variable as a function of time by placing one of the plates of the interferometer on piezoelectric ceramics.

If $e_o$ is the thickness of the initial air layer before actuating the ceramics, and V is a constant speed of displacement of the plate, the light intensity at point F will be I $$I = \frac{T^2}{1-R^2}$$

$$[1 + 2R\cos 2\pi\sigma[2e_o + 2Vt] + 2R^2\cos 2\pi\sigma[4e_o + 4Vt] + \ldots + 2R^n\cos 2\pi\sigma[2e_o + 2nVt]]$$

which is indicative of an interferometric system, with n path difference $\Delta_p$, where $\Delta_p 2pe_o$, p being a whole number between 1 and n, each term being modulated at a different frequency $f_p = 2p\ \pi V$.

Therefore, there will indeed be observed, according to the fixed aim, at the output of the interferometry system, the superposition of n states of interferences corresponding to n path differences, modulated at different frequencies, each gas $g_i$ being characterized by a path difference $\Delta_{c,i}$ and a modulation frequency $f_i$, and therefore a particular wave number $\sigma_i$.

A representation in the diagram $\Delta,\sigma$ as done in FIG. 3 is convenient for explaining the functioning of such a multigas analyzer.

In this diagram, gas $g_1$ can be represented by the region i, actually it absorbs over a region i and causes a regrowth of the fringes around $\Delta_{c,i}$. Likewise be represented by region j. Therefore, it suffices to adjust $e_o$ so that $\Delta_{c,i}$ and $\Delta_{c,j}$ belong to the set of $\Delta_p = 2p\ e_o$.

It is advantageous to select $e_o$ small enough, as a function of the gases it is desired to detect, so that the sampling is closely enough spaced for a regrowth not to pass unnoticed.

Let us note that if two gases absorb in the same region with characteristic different path differences, the data relative to these two gases will be modulated at different frequencies. Therefore it will be easy to separate them by frequency filtering and these combined data received by the same detector will be able to demultiplexed electronically.

If two gases absorb in different regions for the modulation frequencies to be different, it is necessary that $\sigma_i$ x i $\neq \sigma_j$ x j. Therefore, in some cases it will be advantageous to place a network demultiplexer behind the interferometer to isolate the absorption bands of the different gases studied.

An analysis is made of the signal received, a function of the distance between the plates of the interferometer, frequency band by frequency band. For each of the frequency bands, as done above, a study is made of the value of the distance for which the signal exhibits a maximum, and there is deduced directly from it the gas which thus indicates its presence and concentration.

Figure 1:
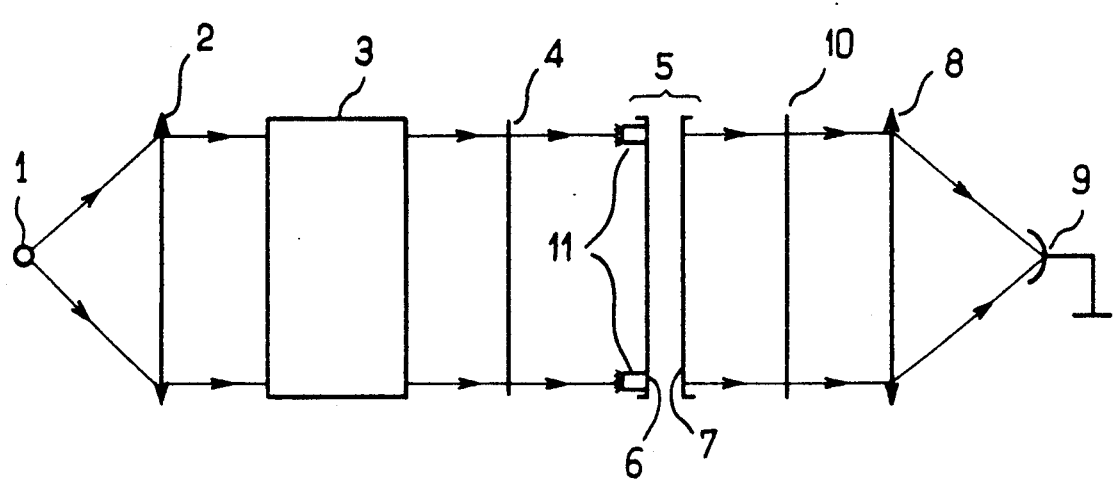
FIG. 1 illustrates diagrammatically the unit of the detection device of the present invention.

An embodiment making it possible to use the process according to the invention is diagrammed in FIG. 1.

Elements similar to those of the prior device are found in this device, although their use is not the same.

The device according to the invention comprises a broad spectrum source 1 whose beam is focused by lens 2; goes through gas cell 3; goes through Fabry-Perrot multiple-wave interferometer 5, the inside face of whose plates 6 and 7 is covered with a highly reflective layer and one of whose plates is mounted on piezoelectric cells 11; goes through a focusing lens 8; and reaches an analyzing detector 9.

Secondarily, an interference filter 4 can be placed between gas cell 3 and the multiple-wave interferometer if it is desired to use the multigas analyzer as a monogas analyzer, to isolate the specific spectral band of the gas studied.

In a variant, a network demultiplexer 10 is placed between interferometer 5 and focusing lens 8 to isolate the absorption bands of the different gases studied. The preferred embodiment of the multigas analyzer does not comprise either this filter 4 or this network demultiplexer 10.

As a function of existing materials, it is possible to envisage making a device with different technology, depending on whether it is intended for studies in the infrared or ultraviolet.

Thus, for example, for a device intended for analyses other than in the infrared region, the source can be a globar; the lenses, windows of the cell and interferometer plates of fluorine; the reflecting layers of the interferometer of silica; and the detector a cooled PbSe photo-resistant cell. resistant cell.

The distance between the interferometer plates will be adjusted, for example, at 1 mm. The travel permitted by the piezoelectric cells being only a few tens of microns, the latter will be subjected to a "sawtooth" voltage gradient so that the mobile plate of the interferometer will undergo not a continuous displacement at constant speed, but a back-and-forth movement between two positions, the forward displacement being performed at constant speed, always the same.

Of course, the invention is not limited to the embodiments described and represented and it is capable of numerous variants accessible to one skilled in the art, without going outside the spirit of the invention.

What is claimed is:

1. A process for simultaneous detection of several gases contained in a gaseous mixture, which gases exhibit a quasi-periodic absorption spectrum, comprising the steps of:
   providing a broad spectrum light beam through the gaseous mixture to cause an incident ray to fall upon an interferometry and modulation unit;
   producing at least three parallel transmitted rays from said incident ray within said interferometry and modulator unit, each of said transmitted rays having vibrations exhibiting, relative to said incident ray, a path difference which is a different multiple of an elementary path difference;
   modulating said vibrations corresponding to each of said transmitted rays at different by varying the elementary path difference;
   focusing said transmitted rays to form a signal;
   detecting and recording said resulting signal;
   frequency filtering said resulting signal; and
   analyzing the intensity of said resulting signal, frequency band by frequency band.

2. An interferometric detector for the simultaneous detection of several gases contained in a gaseous mixture, comprising: a light source propagating a beam, said beam successively passing through a concentration lens, a gas cell, and an interferometry and modulation unit before reaching a detection cell; said interferometry and modulation unit including a multiple-wave interferometer having a pair of planar parallel plates, each of said plates having an interior face, said interior faces of said plates being disposed opposite to one another, each said interior face being covered by a reflecting layer with a reflection coefficient greater than 0.5, wherein at least one of said plates is mounted on a piezoelectric cell for displacement at a constant speed.

3. The detector according to claim 2, further comprising a grid system demultiplexer, said demultiplexer being situated between said multiple-wave interferometer and said detection cell to isolate the absorption bands of different gases studied.

4. The detector according to claim 2, further comprising an interference filter situated between said gas cell and said interferometry and modulation unit.

5. An interferometric detector for the simultaneous detection of several gaseous contained in a gaseous mixture, comprising a light source propagating a beam, said beam successively passing through a concentration lens, a gas cell, an interferometry and modulation unit, and a focusing lens, before reaching a detection cell; said interferometry and modulation unit including a multiple-wave interferometer having a pair of parallel planar plates, each of said plates having an interior face, said interior faces being disposed opposite to one another, each said interior face being covered by a reflecting layer with a reflection coefficient greater than 0.5, and wherein at least one of said plates is mounted on a piezoelectric cell for displacement at a constant speed.

6. The detector according to claim 5, wherein a grid system demultiplexer is placed between said multiple-wave interferometer and said detection cell.

7. The detector according to claim 5, wherein an interference filter is placed between said gas cell and said interferometry and modulation unit.

* * * * *